United States Patent
Smaal

(10) Patent No.: US 10,420,329 B2
(45) Date of Patent: Sep. 24, 2019

(54) METHODS AND SYSTEMS IN EGG HATCHING

(71) Applicant: Viscon B.V., s-Gravendeel (NL)

(72) Inventor: Bastiaan Arie Smaal, s-Gravendeel (NL)

(73) Assignee: Viscon B.V., S'-Gravendeel (NL)

( * ) Notice: Subject to any disclaimer, the term of this patent is extended or adjusted under 35 U.S.C. 154(b) by 248 days.

(21) Appl. No.: 15/509,321

(22) PCT Filed: Aug. 3, 2015

(86) PCT No.: PCT/NL2015/050564
§ 371 (c)(1),
(2) Date: Mar. 7, 2017

(87) PCT Pub. No.: WO2016/039622
PCT Pub. Date: Mar. 17, 2016

(65) Prior Publication Data
US 2017/0238510 A1    Aug. 24, 2017

(30) Foreign Application Priority Data
Sep. 8, 2014 (NL) ...................................... 2013435

(51) Int. Cl.
*A01K 41/00* (2006.01)
*A01K 41/06* (2006.01)
*A01K 43/00* (2006.01)
*A01K 31/00* (2006.01)
*A01K 45/00* (2006.01)
(Continued)

(52) U.S. Cl.
CPC ............ *A01K 41/00* (2013.01); *A01K 31/002* (2013.01); *A01K 41/065* (2013.01); *A01K 43/00* (2013.01); *A01K 45/005* (2013.01); *G01N 21/59* (2013.01); *G01N 33/085* (2013.01); *G01N 2201/061* (2013.01)

(58) Field of Classification Search
CPC .... A01K 41/00; A01K 31/002; A01K 41/065; A01K 43/00; A01K 45/005; A01K 43/04; A01K 43/06; A01K 43/08; A01K 43/10; G01N 33/085; G01N 33/08; B65G 47/90; B65G 49/05
See application file for complete search history.

(56) References Cited

U.S. PATENT DOCUMENTS

| 5,898,488 A | 4/1999 | Kuhl |
| 2009/0078205 A1* | 3/2009 | Hebrank ................ A01K 43/00 119/6.8 |

(Continued)

FOREIGN PATENT DOCUMENTS

WO    WO-2014126466    8/2014

*Primary Examiner* — Trinh T Nguyen
(74) *Attorney, Agent, or Firm* — Marcus C. Dawes

(57) ABSTRACT

The present disclosure relates to methods and systems in egg hatching, based on hatching eggs in a tray (2), comprising arranging eggs in a pattern in or on the tray, comprising egg supporting positions and holes together defining the pattern, wherein the holes are dimensioned to allow chicks (27) after hatching to pass there through into a crate (4), detecting at least one of numbers of unhatched eggs (22) in or on the tray; numbers of dead chicks in the crate; and numbers of objectionable chicks in the crate, and supplementing or removing chicks to or from the crate in correspondence therewith.

3 Claims, 8 Drawing Sheets

(51) Int. Cl.
    *G01N 21/59*    (2006.01)
    *G01N 33/08*    (2006.01)

(56) References Cited

U.S. PATENT DOCUMENTS

| | | | |
|---|---|---|---|
| 2009/0314691 A1* | 12/2009 | Hebrank | A01K 43/00 |
| | | | 209/511 |
| 2014/0205422 A1 | 7/2014 | Mogenet | |
| 2015/0071741 A1* | 3/2015 | Schnupper | A01K 43/00 |
| | | | 414/225.01 |
| 2015/0138537 A1* | 5/2015 | Yamamoto | A01K 43/00 |
| | | | 356/53 |
| 2015/0166267 A1* | 6/2015 | Suh | A01K 45/007 |
| | | | 414/416.01 |
| 2016/0227744 A1* | 8/2016 | Rees | A01K 43/00 |
| 2017/0210571 A1* | 7/2017 | Suh | A01K 41/06 |
| 2017/0265439 A1* | 9/2017 | Meter | A01K 41/065 |

* cited by examiner

METHODS AND SYSTEMS IN EGG HATCHING

The present disclosure relates to methods and systems in the field of egg hatching.

Egg hatching is performed during a specific period of production of young chickens or any arbitrary other type of poultry. Examples herein below will be provided on the basis of production of chickens, but it should be clear that the scope of protection is by no means limited to any type of specific poultry. Production is initiated by gathering fertilised eggs. In fact, normally all eggs are gathered, and fertilised ones of the gathered eggs are selected and stored for a predetermined period in for instance an incubator. In the case of chickens, eggs are stored in an incubator during for example 18 or 19 days. Thereafter the relevant specific period of egg hatching is initiated.

Previously, eggs originating from the incubator were transferred into a hatching crate, and left to hatch. After a predetermined time of for instance three days, hatched chickens were extracted, by emptying the crate into a separator which caused considerable stress in the young animals. Subsequently, predetermined numbers of extracted young animals were put, by the separator or any other system component, into a transport crate, again causing considerable stress. Normally, a transport crate was filled to contain a predetermined number of eggs in correspondence with a number of chicks, as agreed on with a chicken farmer/customer, or in accordance with a standard, for example 80 or 90 chicks per transport crate, without any relation between the number of chicks in the transport crate and a number of chicks in the hatching crate.

Based on the shortcomings of previous methods and systems, a need arose to rationalise chicken production processes and reduce stress that was induced in young animals. To this end, newer methods and systems have replaced the traditional hatching crate and transport crate by a combination of a crate and an eggs supporting tray, for example wherein the eggs supporting tray is arranged on top of the crate and comprises holes to allow hatched chicks to enter into the crate of the combination, which could thereafter be used immediately as a transport crate, since eggshell practically entirely remains on the egg supporting tray, after the chicks have hatched. However, such newer methods and systems pose new problems in terms of automation, with respect to arranging unhatched eggs on the egg supporting tray comprising the through holes as well as determining numbers of chicks to be added to the content of the combined chick catching and transporting crate in accordance with the standard or agreement with the chicken farmer/customer. These issues all relate to implementation of the newer systems and methods, in which trays need to be filled, except on positions of holes, and arranged on the crates, that may serve both for hatching and transport but to which chicks in beforehand unknown numbers need to be added or from which a before unknown number of chicks needs to be removed to comply with a filling in accordance with an agreement with a chicken farmer/customer, for which the original degree of filling of the tray—except on positions of holes—would normally have to be considered as a first and very important parameter in combination with numbers of unhatched eggs after the hatching period and numbers of chicks, that have hatched but have died during the hatching period or that are otherwise discarded as unfit for delivery to the chicken farmer/customer.

In this context reference is made here to the prior art publication of WO-2014/126466, which is considered to constitute the closest prior art in relation to the present disclosure, which is silent about filing of eggs in hatching crates and about supplementing or removing good chicks in hatching crates to enable the use of hatching crates as transport crates and reduce overall stress of young animals. Further, US-2014/0205422 is acknowledged here, which teaches—without any relation with pattern of holes of crates—that it is possible to deposit eggs selectively at locations where eggs are missing.

The present disclosure is aimed at improving the combined technical feasibility of the newer methods and systems. To this end, methods according to the appended independent method claims and systems according to the appended independent system claims are provided.

According to a first aspect of the present disclosure, arranging of the eggs in the tray according to the present hatching method comprises: dividing the pattern into a plurality of constituent lines of eggs, together forming the pattern; engaging eggs in at least one row of eggs corresponding to at least one of the plurality of constituent lines of eggs; depositing the at least one row of engaged eggs along the at least the corresponding one of the plurality of constituent lines; and repeating the steps of engaging the eggs in at least one row and depositing the at least one row of engaged eggs until the pattern of eggs in or on the tray is filled with eggs. In particular according to this aspect of the present disclosure, a very elegant and simple method can be provided, according to which complex programming of patterns of eggs at, near or around holes in the tray can be avoided, and allows the use of very simple transporters. For example a single transport can be driven twice to engage rows of eggs and deposited the eggs along the constituent lines, whilst alternatively to a very simple transporters can be driven, each one's, to perform the same task. By dividing complex patterns into constituent lines, a considerable simplification of the partial process of depositing eggs in the desired complex patterns can be achieved.

It is noted here that the disclosure of US-2014/0205422 relates essentially to filling trays having only a pattern of egg supporting positions, but no holes, and is silent about constituent lines. This publication teaches depositing all missing eggs in one pass, even if a tray is initially completely empty, and since any pattern of a tray consists only of egg supporting positions, the basic approach is directed at and based on the entirety of the pattern. The skilled person doesn't derive from this publication any incentive to consider division of the pattern into constituent lines, since therefrom the skilled person doesn't derive any need for or beneficial effect from division of the pattern into constituent lines.

According to the second aspect of the present disclosure, the method may additionally comprise processing of chicks in the crate, where said processing may comprise detecting, after lapse of the predetermined time, at least one of the parameters from the group, comprising: numbers of unhatched eggs in or on the tray; numbers of dead chicks in the crate; and numbers of objectionable chicks in the crate, and supplementing chicks to the crate in correspondence with at least any one or more than one of the detected numbers.

The objectionable chicks in the crate have hatched, and could be sick or weak. Automatic detection can be employed, for instance based on the vision system, to isolate and extract such objectionable chicks.

More importantly, based on prior knowledge of the numbers of eggs, arranged in or on the tray in egg supporting positions thereof, around the holes, after the hatching period a number of chicks to be added into or removed from a crate before transport to a chicken farmer/customer can be determined based on the above-mentioned parameters. Thereby, it is avoided that all chicks are ejected from a hatching crate and transferred to a separate transport crate, whereby all the chicks are subjected to the considerable stress of transfer into another crate for transport. The final chick count per crate could be the same as the number of unhatched eggs to be arranged in or on the tray prior to the hatching period, or could be any other number. Any difference between the desired number of chicks per transport crate and a number of eggs to be accommodated in or on the tray, can be taken as a default value for a number of chicks to be added to or extracted from the crate, to enable use of the hatching crate for transport, i.e. as a transport crate. For instance, if the tray can accommodate 90 eggs and each crate should contain 80 chicks, then 10 chicks need to be extracted from the crate, if all of the eggs have hatched at the end of the hatching period and all the chicks are alive and healthy. Also, if a tray can hold 85 eggs, and the crate should contain 80 chicks, whereas normally on average five eggs do not hatch, the number of chicks to be extracted or added will—on average—be zero. However, the numbers of chicks per crate need to be accurate for each crate and not on average. With prior knowledge about the number of eggs on each tray, the total number of chicks per crate does not need to be counted, but surprisingly it suffices to only determine a number of unhatched eggs, numbers of dead or otherwise unsuitable chicks. This simplifies considerably the process portion of having to ensure that a predetermined number of chicks is provided in each crate, wherein such a crate is used during the hatching period and thereafter for transport, and the amount of stress for the young animals is considerably reduced by this simplification. Additionally it is to be noted in this respect that the fill amount in terms of numbers of chicks may be made higher than normal (for example 100 chicks instead of 80 per crate) to increase transport efficiency. For the purpose of transport, any feed cups, if provided, may be filled with more feed than if the crate is not intended to be transported.

After the above indication of the concept according to the present disclosure in more generic terms, the dependent claims define aspects and preferred embodiments of the concept according to the present disclosure in more specific terms, where such aspects and preferred embodiments are also subject of the below figure description where reference is made to the appended drawing. However, such aspects and preferred embodiments of the dependent claims and/or the specific figure description are by no means provided to allow an interpretation of the scope of protection according to the present disclosure as being limited to any such specific aspects or features.

In a preferred embodiment of a hatching method of the present disclosure, the lines are straight lines. Consequently very simple configurations of transporters, for instance but not exclusively comprising suction cups, allow very complex configurations of egg supporting positions in or on the trays relative to the holes therein, like honeycomb arrangements of the eggs around the holes in or on the tray, and such arrangements of eggs can very simply and elegantly be constituted from the referenced straight lines, even though the resulting configuration is relatively complex in terms of adaptation of transporters and programming thereof.

In a preferred additional or alternative embodiment of the present disclosure, a hatching method comprises simultaneously engaging eggs in at least two rows corresponding to at least two lines, and simultaneously depositing the simultaneously engaged at least two rows of eggs. In such an embodiment, preferably but not limited thereto, the lines are parallel. By engaging eggs in at least two rows simultaneously, these can also be simultaneously deposited in or on the tray along the constituent lines or at least a number thereof. When the lines are parallel, two passes by a single transport or one pass by each of a couple of transporters can suffice to completely fill the tray, wherein rows of eggs are deposited along oblique or orthogonal sets of lines. Consequently, practically any pattern of eggs in or on the trays can be deposited very simply and elegantly, regardless of the complexity of the resulting pattern.

In a preferred additional or alternative embodiment of the present disclosure, a hatching method comprises the feature that at least one of the plurality of lines is positioned oblique or essentially perpendicular relative to at least one other of the plurality of lines. Therefore, oblique or essentially perpendicular or even orthogonal positioning of lines or sets of lines can be implemented, even if the lines are not straight, or if less than two rows of eggs are deposited at any one time or during one pass of one or more than one transporter.

In a preferred additional or alternative embodiment of the present disclosure, a hatching method comprises the feature that all parallel groups of rows of eggs are deposited along all corresponding parallel lines in a single depositing step. This feature allows that a maximum of two passes is required for depositing all of the eggs in or on the tray, regardless of the complexity of the resulting pattern.

In a preferred additional or alternative embodiment of the present disclosure, a hatching method comprises the feature that detection of unhatched eggs comprises, after lapse of the predetermined period, illuminating at least one egg supporting position of a tray and monitoring transmission and/or reflection of illumination and determining the presence of an unhatched egg depending on the monitored transmission and/or reflection. In such an embodiment, detection of unhatched eggs is realised in a simple and elegant manner, which may even be combined with detection of live embryos (candling) within the eggs in a step prior to the hatching period. In such an embodiment, the additional feature can be provided that illuminating at least one egg support position comprises illuminating the egg support position using IR light. In particular infrared light is known to be allowed detection of an even a heartbeat of an embryo within an egg.

In a preferred additional or alternative embodiment of the present disclosure, a hatching method comprises the feature of: candling eggs prior to arranging the eggs in the pattern in or on the tray, for instance using IR light, to determine whether embryo's in eggs are viable or dead, and rejecting dead or unviable eggs.

Further it is noted here that the present disclosure also relates to systems that may be configured to execute the methods according to the present disclosure.

After the above description of the subject matter of the present disclosure in more generic terms in accordance with the appended claims, herein below specific embodiments will be described, referring to the appended drawings. Therein, the same or similar elements, components and aspects may be referred to using identical or similar reference numbers, regardless of the different embodiments in which these reference numbers are used, to indicate that the function or effect thereof is essentially the same for the different embodiments, in which these elements, components and aspects are applied. Further it is noted, that the following embodiment description will comprise reference to specific elements, components and aspects, whereas the appended claims and in particular the appended independent claims may refer to more generic indications or features, and that the more specific elements, components and aspects below are by no means to be interpreted as limiting on the scope of protection of the present disclosure. In the drawing:

Figure 3:
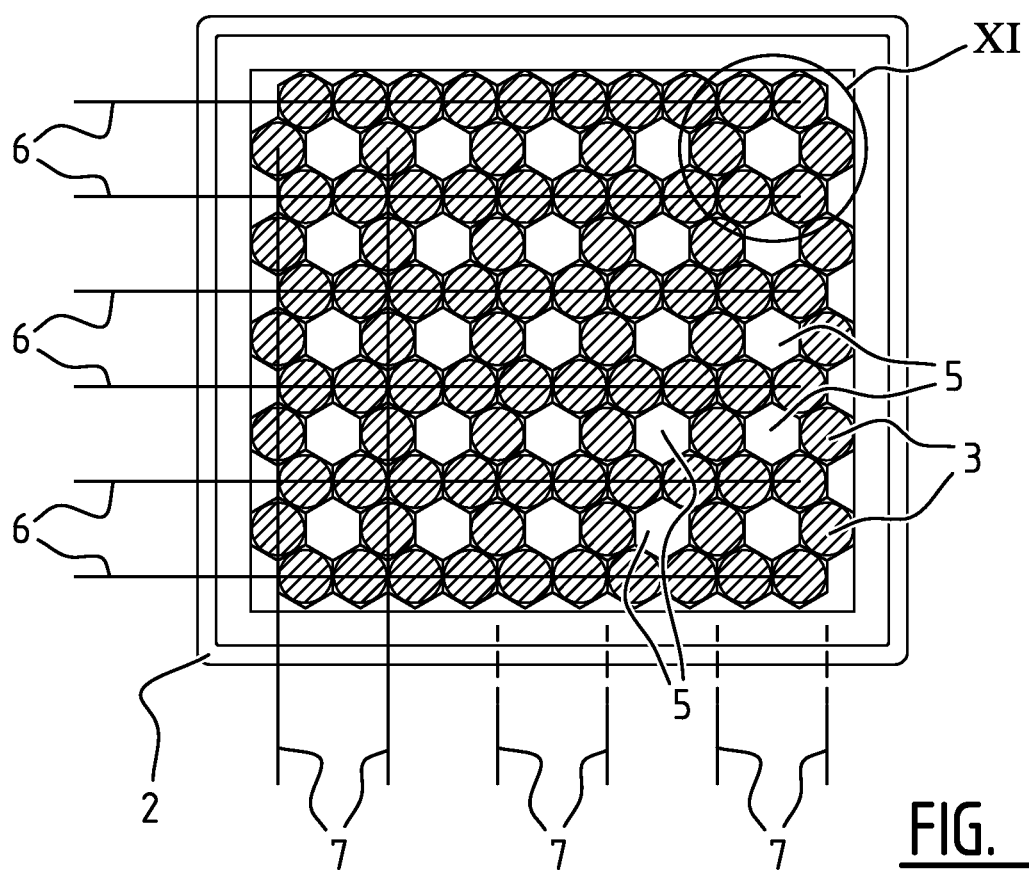
FIG. 3 shows a top view of the tray along arrow III in FIG. 1, identifying a plurality of groups of lines corresponding with which rows of eggs to be deposited.
Figure 4:
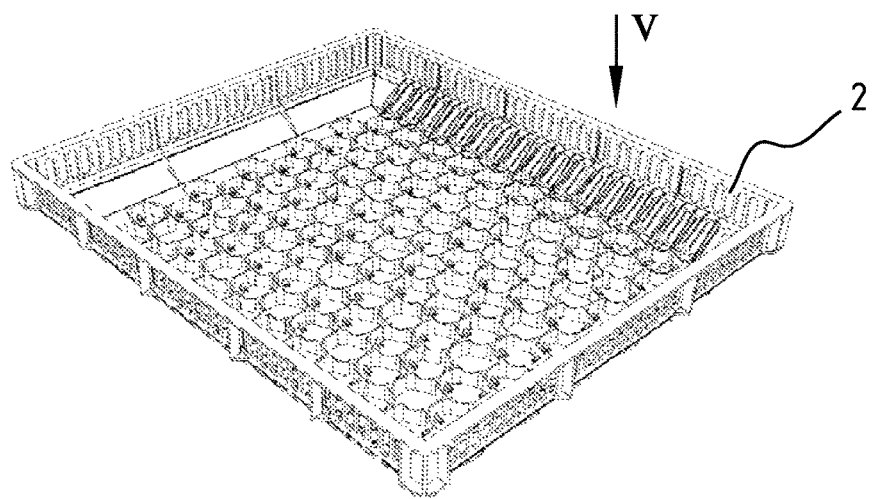
FIG. 4 shows a perspective view of the hatching tray in isolation, that may be used to accommodate unhatched eggs in the hatching period.
Figure 5:
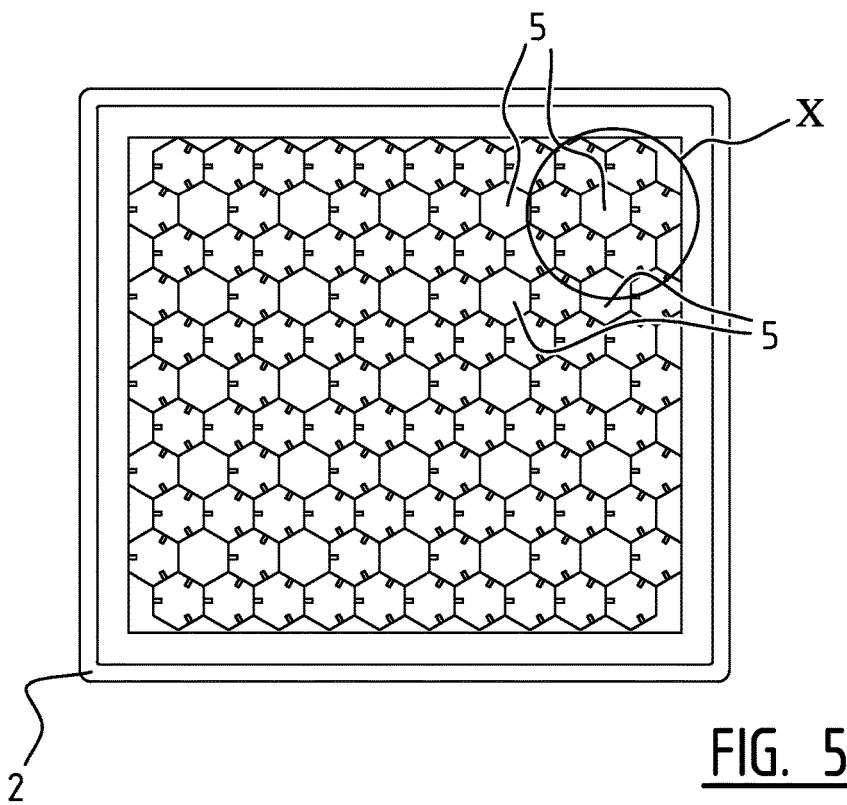
FIG. 5 shows a top view in the direction of arrow V on the hatching tray in FIG. 4.
Figure 8:
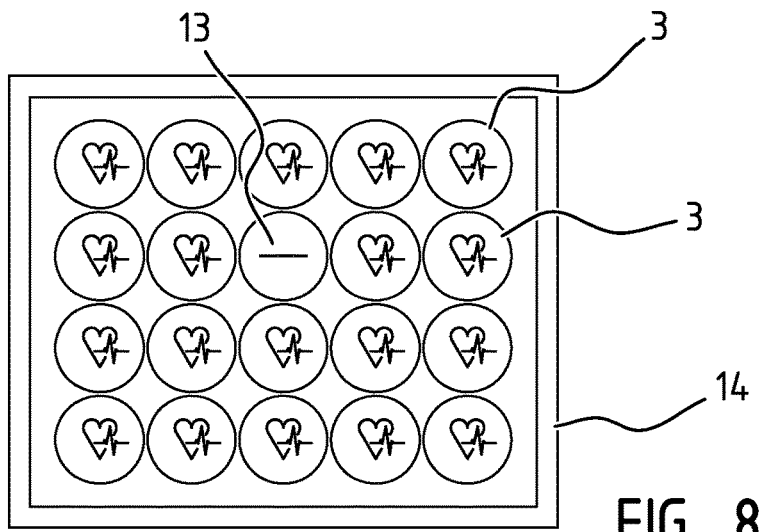
Figure 9:
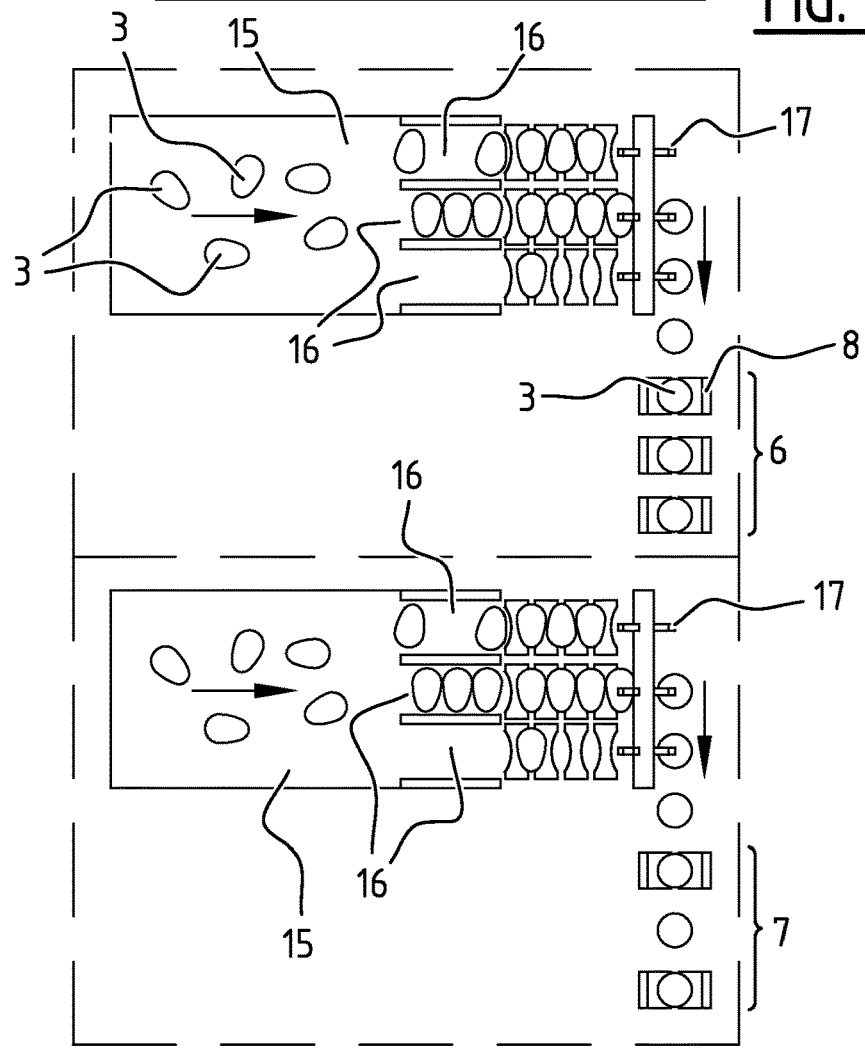
Figure 10:
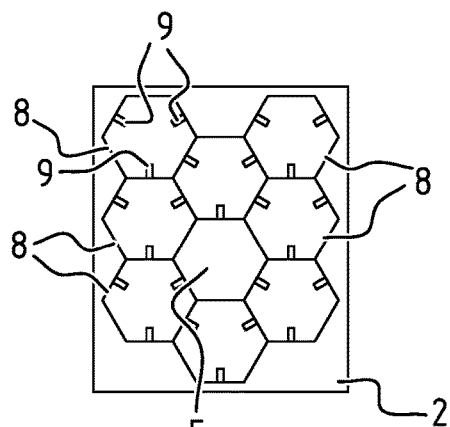
Figure 11:
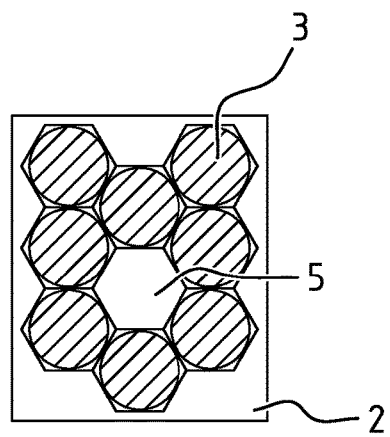
Figure 12:
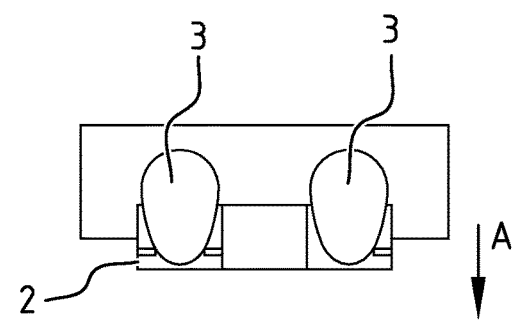
Figure 13:
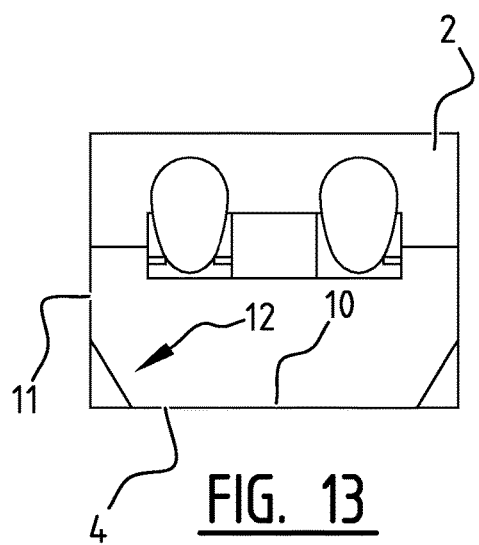
Figure 14:
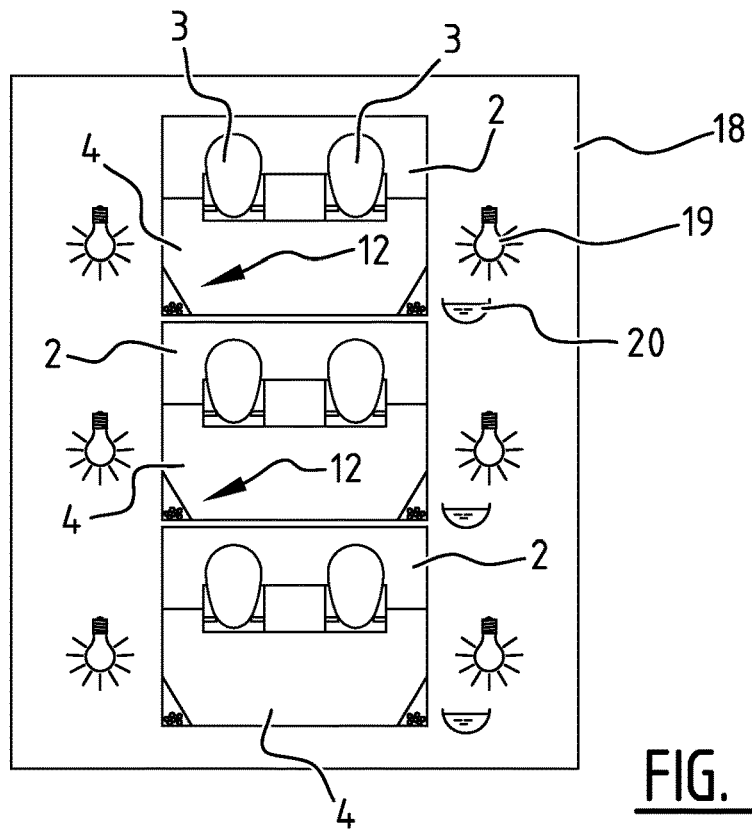
Figure 15:
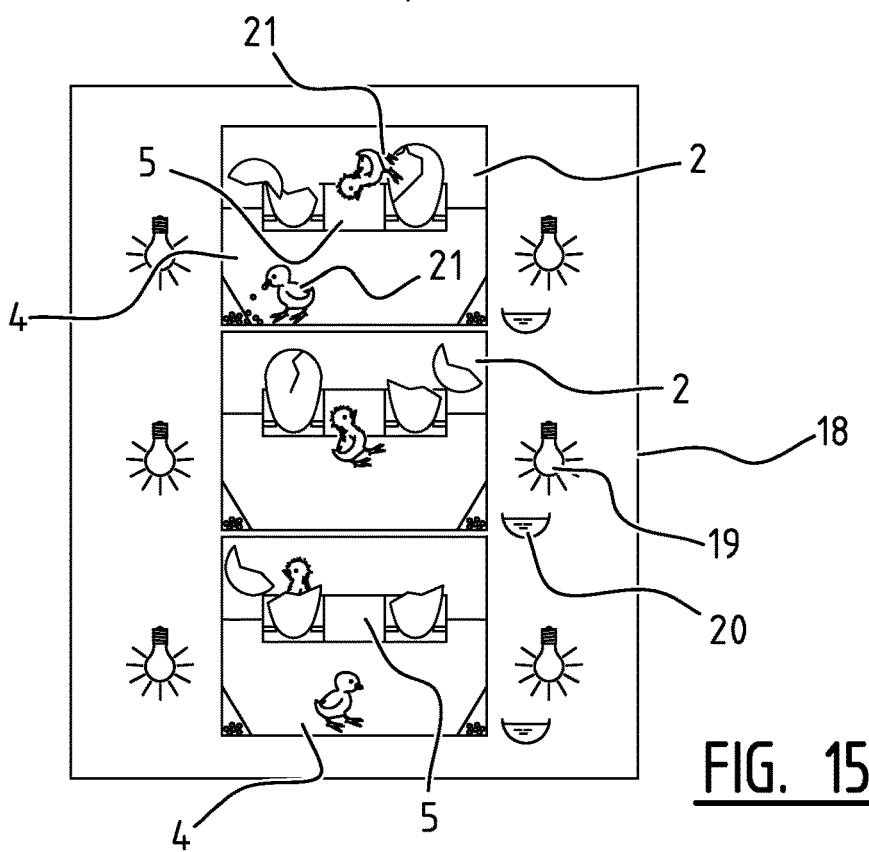
Figure 16:
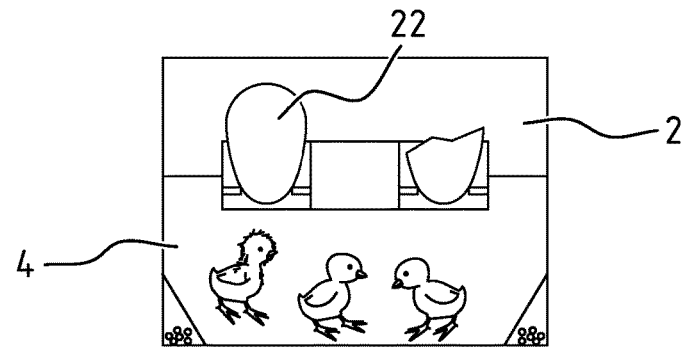
Figure 17:
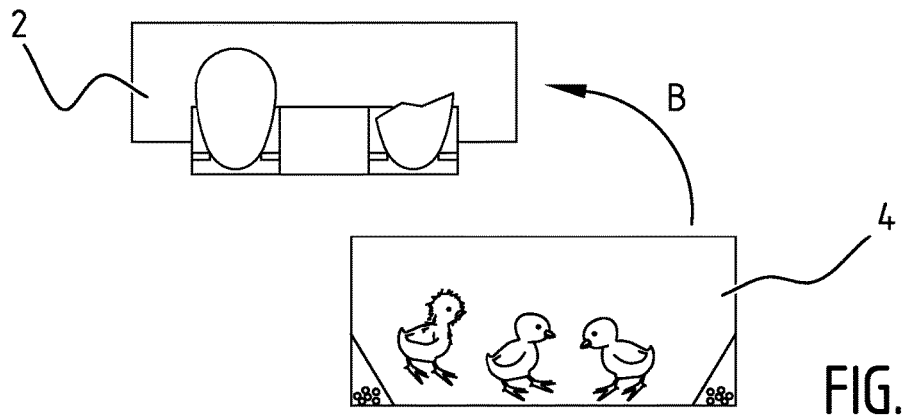
Figure 18:
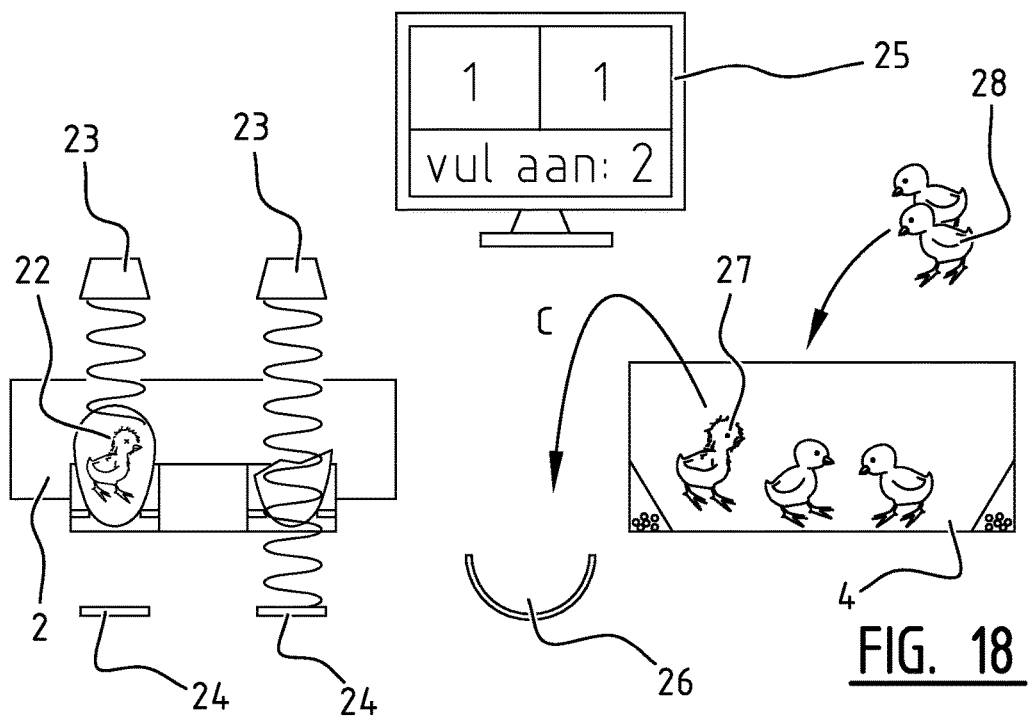

FIG. 8 schematically represents the outcome of candling in a step, prior to a hatching period;

FIG. 9 schematically represents the manner in which groups of rows of eggs, corresponding with the lines described in association with FIG. 3, may be formed;

FIG. 10 shows a detail X from FIG. 5;

FIG. 11 shows a detail XI from FIG. 3;

FIG. 12 shows a simplified, schematic representation of assembly of the transport crate and the hatching tray in a potential embodiment of the present disclosure; and FIG. 13 shows an assembled state of the transport crate and hatching tray of FIG. 12;

FIG. 14 shows a schematic representation of storage of a plurality of assembled crate and tray combinations of FIG. 13 during the hatching period;

FIG. 15 shows a schematic representation of how hatched chicks practically automatically drop through holes in the trays to be accommodated in the transport crates for the rest of the duration of the hatching period;

FIG. 16 shows a schematic representation of the situation, where at the end of the hatching period, a single egg in an egg supporting position has not hatched, which can be easily determined using for instance infrared or any other type of light, combined with detection of transmission or reflection characteristics at the egg supporting position, which may be repeated for each of the egg supporting positions of a tray;

FIG. 17 schematically shows a step of de stacking one combination of a transport crate and a hatching tray; and FIG. 18 schematically shows a step in the process of supplementing numbers of chicks in a transport crate, based on detection of a number of unhatched eggs in a hatching tray after the end of the hatching period.

Figure 1:
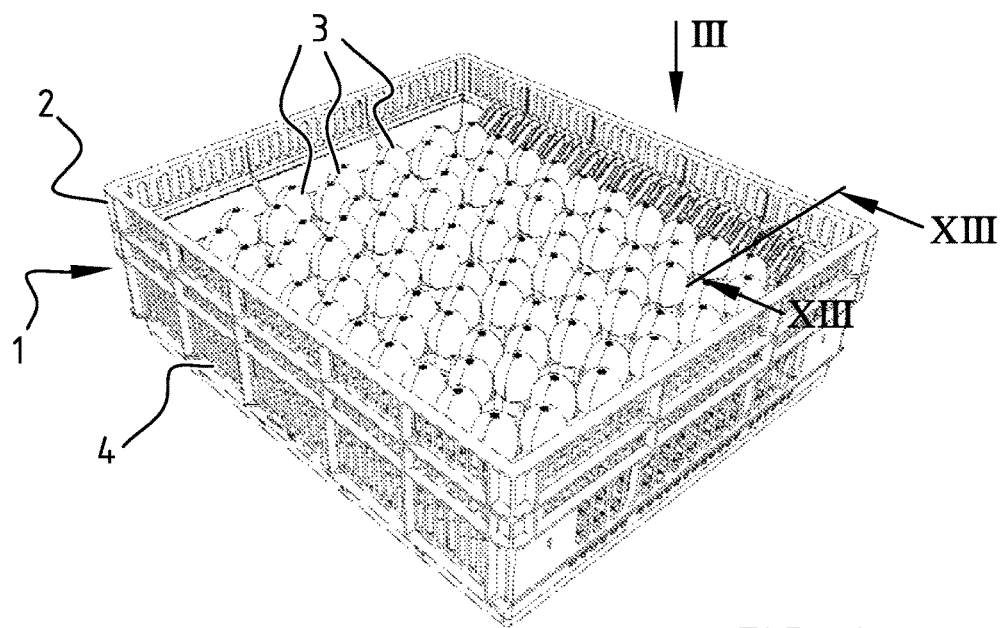
FIG. 1 shows a perspective view of a combination of a transport crate and a hatching tray, filled with eggs.
Figure 2:
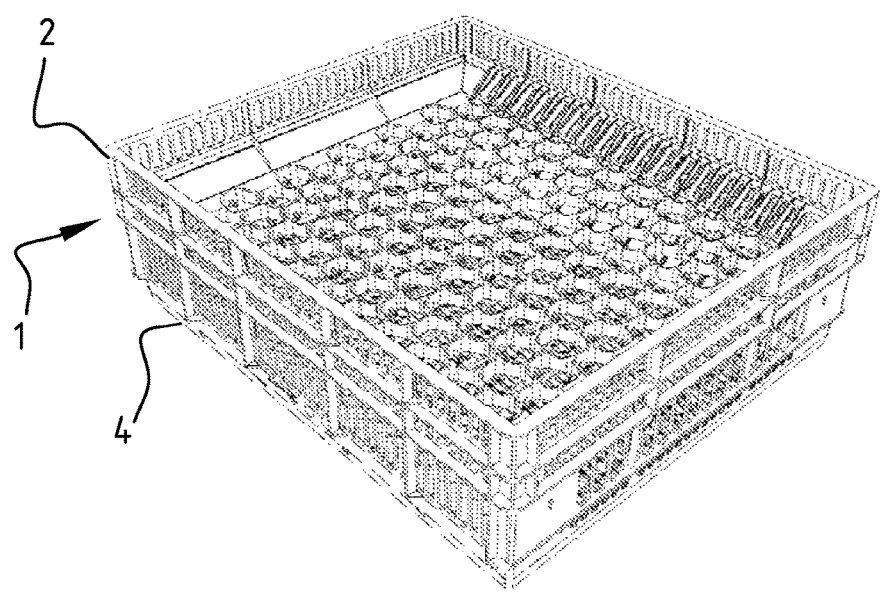
FIG. 2 shows a perspective view of a combination of a transport crate and a hatching tray, without any eggs.

FIGS. 1 and 2 show in respective views on a combination 1 of a hatching tray 2 and a hatching or transport crate 4. In the representation of FIG. 1, eggs 3 are accommodated in the hatching tray 2, whereas these eggs 3 have been omitted in the representation of FIG. 2. FIG. 3 shows a top view along arrow III in FIG. 1 on the field hatching tray. Therein, drop holes 5 are clearly visible, surrounded by eggs 3 in honeycomb patterns. Drop holes 5 are dimensioned to allow hatched chicks to drop from the upper lying tray 2 into the underlying crate 4. Honeycomb patterns and many other patterns are near impossible to create, using conventional transporters, for instance transport heads comprising a matrix of suction cups, in particular because of the offset of certain specific egg supporting positions of tray 2, relative to the pure matrix form of the referenced conventional transporters with a matrix of suction cups.

As indicated in FIG. 3, the pattern, and in this case the honeycomb pattern, of a group supporting positions of the tray 2 surroundings through holes 5 is divided into A. straight lines 6, associated with rows of adjacent egg supporting positions of the tray 2 along the straight lines 6, and B. straight lines 7 associated with rows of spaced egg supporting positions of the tray 2 along the straight lines 7. It is considered self evident, that lines 7 are offset relative to a pure matrix form, if based on the rows of eggs and the lines 6 associated there with, or vice versa.

Division of the complex form of the patterns into straight lines 6, 7 allows for a single suction head to be loaded twice and pass twice over the hatching tray 2 for accommodating eggs 3 in all of the egg supporting positions. Alternatively, the division of complex patterns into lines 6, 7 allows for using two transporters, each having their own line based pattern of for instance suction cups to fill the hatching tray 2 completely, with the exception of the drop holes 5, in two passes of the different transporters. Further, the division of a complex pattern does not need to be based on the straight lines, but the lines may even be meandering within any one or more than one of the groups of lines, but it seems of importance that the groups of lines are at least oblique if not perpendicular or orthogonal relative to one another, in order to maximally generate a desired deposition of eggs in or on the hatching tray 2 and more in particular in the egg supporting positions thereof, which surround the drop holes 5.

FIGS. 4, 5, 10 and 11 relate to features of the hatching tray 2 in a specific embodiment. Therein, each egg supporting position 8 comprises at least two and preferably three cams or notches 9, four eggs 3 to rest on during the hatching period.

Figure 6:
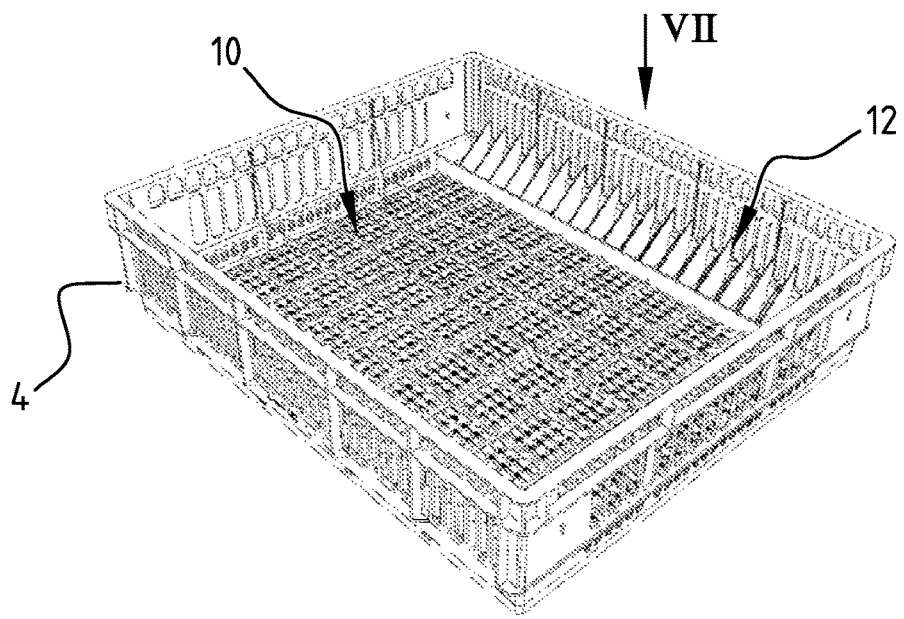
FIG. 6 shows a perspective view of the transport crate in isolation, that may be used to accommodate hatched chicks in the hatching period and thereafter during transport.
Figure 7:
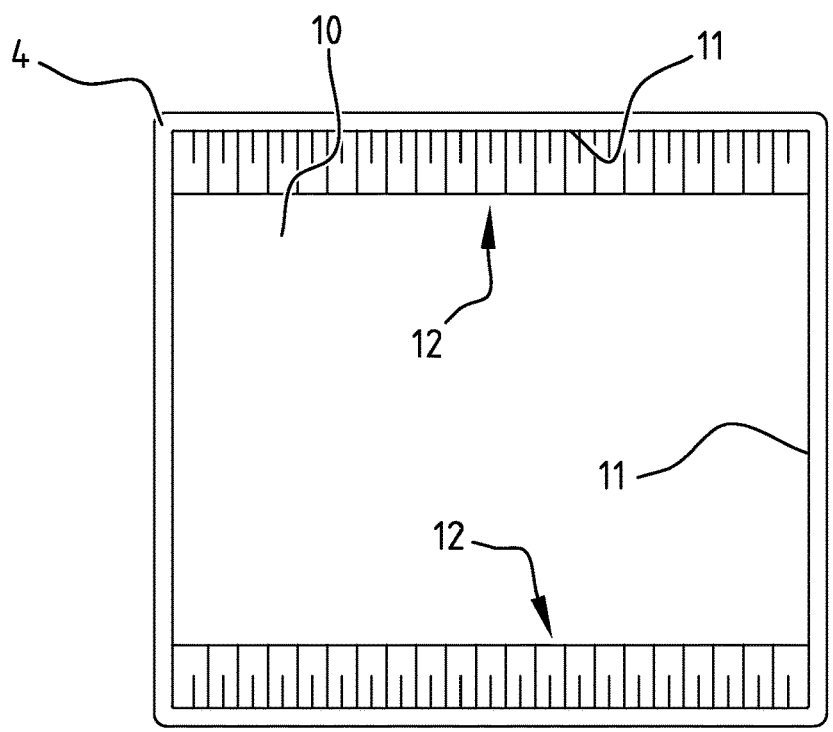
FIG. 7 shows a top view in the direction of arrow VIII on the transport crate in FIG. 6.

FIGS. 6, 7 show in more detail respectively a perspective view and a top view of the hatching and/or transport crate 4. The hatching and/or transport crate 4 comprises a bottom 10 and upright sides 11, with feeding cups 12 for food and/or water of hatched chicks along at least one side wall 11 on the bottom 10. The feeding cups 12 improve animal well-being in that chicks that hatch early can take nourishment. For the purpose of transport, feeding cups 12 may be filled with more feed than usual or normal for situations wherein the crate is not intended to be transported, but the chicks are locally nurtured to develop and grow after hatching.

FIG. 8 shows that the stream of provided eggs can be tested for life, in advance of depositing the eggs 3 in or on the hatching tray 2. In the shown representation, just a single egg 13 does not exhibit a heartbeat, and is ejected or extracted before filling the hatching tray 2. In the representation of FIG. 8, a supply tray 14 is used, which might be an incubator tray that is stored in an incubator cell or storage for a first for instance 18 days. After reaching an age of 18 days, the eggs are taken out of storage in the supply tray or incubator tray 14, and subjected to candling or any other type of check or monitoring to determine whether or not an embryo inside of the eggs three, 13 is alive or dead, which does not necessarily involve monitoring a heartbeat. However, it does appear to be very efficient to test eggs 3, 13, when still in a supply tray or incubator tray 14.

In any case, after extracting or ejecting eggs 13 with dead embryos, in accordance with the schematic representation of FIG. 9, the remaining live eggs 3 are placed on one of two transport belts 15, divided over channels 16, and gripped by grippers 17 to be deposited in egg supporting positions 8 of hatching tray 2. The top half section of the schematic configuration of FIG. 9 deposits eggs 3 in adjacent or neighbouring egg supporting positions 8. This corresponds with lines 6 in FIG. 3 indicating rows of adjacent eggs. In contrast, the bottom half section of the schematic configuration of FIG. 9 deposits eggs 3 in egg supporting positions 8 at intermediate distances, corresponding with the offset lines 7 and the rows of eggs 3 associated with lines 7. Consequently a two stage and very convenient system of depositing eggs in all the desired positions is provided on the basis of a division beforehand into lines, along which rows of eggs need to be deposited.

After filling hatching trays 2 with eggs 3, hatching trays 2 are lowered onto hatching and/or transport crates 4, as indicated with arrow A in FIG. 12, to arrive at an assembled state as depicted in FIGS. 1, 3 and 13. Assembled combinations of crates 4 and trays 2 are stacked and stacks of such combined crates and trays are put in a climate cabin 18 during the hatching period, as shown in FIG. 14. The climate cabin comprises light 19, and/or heating and/or cooling (not shown). Further, the climate cabin may comprise a separate water supply 20 for hatched chicks. In the climate cabin, circumstances are created, which are preferably both beneficial for eggs, which are just about to hatch, as well as young hatched chicks. During the course of the hatching period, more and more of the eggs 3 will hatch, as indicated in FIG. 15. Hatched chicks 21 are in a very confined space on top of the hatching trays 2, especially with combinations of crates 4 and trays 2 immediately above. Consequently, hatched chicks 21 will soon find the drop hole 5, fall through, and remain on the bottom of the hatching and/or transport crate 4 during the remainder of the hatching period, where an amount of food is available in feeding cups 12 and what is available at water supply 20.

Eggs are expected to hatch shortly after 18 days, but mostly before 21 or 22 days. The hatching period, referred to in this disclosure, can therefore be defined as the period between 18 and 22 days for chickens. For other poultry, this hatching period may be different. If, at the end of the hatching period, an egg 22 has not hatched, as shown in FIG. 16, this unhatched egg is removed in the direction of arrow B from the transport and/or hatching crate 4 with egg shell remains of eggs that have hatched, as shown in FIG. 17.

After chicks 21 have hatched from eggs 3, egg shell rests remain on the hatching tray 2. A minimum amount of egg shell is expected to find its way to the bottom 10 of the crates 4. Consequently, when trays 2 are de-stacked from underlying crates 4, egg shell rests and unhatched eggs 22 are removed.

Such a removed tray 2 can, in accordance with the principles underlying the representation in FIG. 18, be subjected to automatic inspection to detect a remaining unhatched egg 22, for example by employing an infrared light source 23 and detector 24. Combinations of sources 23 and detectors 24 can be provided at each of the egg supporting positions 8 of tray 2, for detecting all unhatched eggs 22 in one pass. Detection results are transmitted to a control 25, which is schematically represented by a display only, but will most likely comprise a computer or the like. The computer has prior knowledge about the numbers of eggs 3 that have been put into the hatching trays 2. Also, the computer or other control 25 has information regarding the numbers of chicks that are supposed to be included into a transport tray 4 in accordance with an agreement with a chicken farmer/customer or in accordance with the convention or other rules. Based on these two pieces of information, the controller 25 is able to deduce how many young chicks need to be added to or removed from each transport and/or hatching crate 4. The number of eggs in each tray 2 does not necessarily correspond with the desired number of chicks in each crate. Consequently, when a number of unhatched eggs 22 is detected after the stacking trays 2 from crates 4, the control 25 can determine how many chicks need to be added into or removed from each hatching and/or transport crate 4. Therefore, rather than subjecting all of the chicks in a hatching crate to the stress of being moved to another transport crate, numbers of movements of young chicks can be minimised, based upon the principles of the present disclosure. Further, as an addition or an alternative, it is possible to manually or automatically inspect chicks inside a hatching and/or transport crate 4 with respect to deformation, disease and death, to be extracted from the crate and removed along a discharge 26. If this portion of the process is automatic, then the controller 25 can be arranged to take into account also numbers of dead, diseased or deformed chicks 27 when deciding how many approved chicks 28 need to be added to or removed from the contents of transport and/or hatching crate 4.

After the foregoing description of embodiments within the scope of the present disclosure, as defined in the appended claims, it should be noted that the skilled person will be very well capable of devising or developing additional or alternative features, compliant with the principles of the present disclosure and the requirements in terms of features according to the appended claims, in particular the appended independent claims. However, all such additional or alternative embodiments should be interpreted as comprised within the scope of protection according to the principles of the present disclosure under required features according to the appended independent claims, unless such additional or alternative embodiments substantially deviate from the aforementioned principles and/or requirements in terms of features. For instance, for the position of eggs in hatching trays drop holes are in themselves essentially only referred to in order to fully clarify the challenges posed by complex patterns in which eggs are to be deposited in the hatching trays. Further, with respect to the division in sets of lines, in accordance with rows of eggs, to be deposited in or on the hatching trays, it is noted that these do not necessarily need to be straight and can meander, what is of importance to acknowledge that with two or more passes, any pattern of eggs can be deposited in or on hatching trays, regardless of the complexity of the patterns in which the eggs need to be deposited. Thereby the complex patterns are reduced to quite easily manageable patterns, even though a succession of passes of for instance one engaging head using suction cups or any other transport means may turn out to be required as a consequence, and alternatively, to increase filling speed, two or more engaging heads may be employed, where a single such farmpacker or other type of engaging head making multiple passes over the tray and/or the crate, is an embodiment which is by no means excluded from the present invention.

What is claimed is:
1. Hatching method, designed to hatch eggs in at least one tray crate, comprising:
   arranging eggs in or on egg supporting positions in or on the crate;
   allowing a predetermined time for the chicks to hatch; and
   processing chicks in the crate,
   wherein processing chicks in the crate comprises:
      detecting, after lapse of the predetermined time, at least one of the parameters from a group comprising numbers of unhatched eggs in or on the crate, numbers of dead chicks in the crate, and numbers of objectionable chicks in the crate, and supplementing or removing chicks in or from the crate based on any one or more than one of the detected numbers in comparison with a predetermined desired number of chicks in the crate, corresponding with a number of chicks arranged in the crate for transport.

2. Hatching method as claimed in claim 1, wherein the arranging comprises:

dividing the eggs into a plurality of constituent lines of eggs, together forming a pattern;

engaging eggs in at least one row of eggs corresponding to at least one of the plurality of constituent lines of eggs;

depositing the at least one row of engaged eggs along the at least the corresponding one of the plurality of constituent lines; and repeating the steps of engaging the eggs in at least one row and depositing the at least one row of engaged eggs until the pattern of eggs in or on the crate is filled with eggs.

3. System, comprising:

a supply of chicks in at least one crate and of at least one tray, said tray comprising egg supporting positions defining a pattern;

at least one detector connected to a control, together configured to detect at least one of the parameters from a group comprising numbers of unhatched eggs in or on the tray, numbers of dead chicks in the crate, and numbers of objectionable chicks in the crate; and wherein the control is configured to either or both of indicate a number of chicks, and drive a transfer to add or remove said number of chicks in or from the crate in correspondence with any one or more than one of the detected numbers.

* * * * *

UNITED STATES PATENT AND TRADEMARK OFFICE
CERTIFICATE OF CORRECTION

PATENT NO.        : 10,420,329 B2
APPLICATION NO.   : 15/509321
DATED             : September 24, 2019
INVENTOR(S)       : Bastiaan Arie Smaal It is certified that error appears in the above-identified patent and that said Letters Patent is hereby corrected as shown below:

In the Claims

Column 8 Line 58 Claim 1 should read:
Hatching method, designed to hatch eggs in at least one crate, comprising:
    arranging eggs in or on egg supporting positions in or on the crate;
    allowing a predetermined time for the chicks to hatch; and
    processing chicks in the crate,
    wherein processing chicks in the crate comprises:
    detecting, after lapse of the predetermined time, at least one of the parameters from a group comprising numbers of unhatched eggs in or on the crate, numbers of dead chicks in the crate, and numbers of objectionable chicks in the crate, and
    supplementing or removing chicks in or from the crate based on any one or more than one of the detected numbers in comparison with a predetermined desired number of chicks in the crate, corresponding with a number of chicks arranged in the crate for transport.

Signed and Sealed this
Nineteenth Day of April, 2022

Katherine Kelly Vidal
*Director of the United States Patent and Trademark Office*